(12) United States Patent
Chen et al.

(10) Patent No.: US 7,148,052 B2
(45) Date of Patent: Dec. 12, 2006

(54) NUCLEIC ACID ENCODING β-1,3-GLUCANASE FROM LILY

(76) Inventors: Chao-Ying Chen, No. 19-2, Lane 103, Sec. 1, Hsinsheng S. Rd, Da An District, Taipei 106 (TW); Ping-Fu Hou, 4Fl., No. 3-6, Shantung Road, Putz City, Chiai 613 (TW)

( * ) Notice: Subject to any disclaimer, the term of this patent is extended or adjusted under 35 U.S.C. 154(b) by 390 days.

(21) Appl. No.: 10/647,649

(22) Filed: Aug. 26, 2003

(65) Prior Publication Data

US 2005/0048638 A1    Mar. 3, 2005

(51) Int. Cl.
C12N 9/00 (2006.01)
C07H 21/04 (2006.01)

(52) U.S. Cl. .......................... 435/252.3; 435/4; 435/6; 435/69.1; 435/183; 435/200; 435/210; 536/23.2; 536/23.4; 536/23.5; 536/23.7; 530/350

(58) Field of Classification Search ................ 435/4, 435/6, 69.1, 183, 200, 209, 210, 252.3, 320.1, 435/325; 536/23.2, 23.4, 23.7; 530/350
See application file for complete search history.

(56) References Cited

U.S. PATENT DOCUMENTS 6,066,491 A    5/2000 Cornelissen et al.

FOREIGN PATENT DOCUMENTS

WO    WO 92/16632    10/1992

OTHER PUBLICATIONS

Didierjean et al. "Heavy-metal-responsive genes in maize: identification and comparison of their expression upon various forms of abiotic stress." *Planta* (1996) 199: 1-8.
Renault et al. "β-1,3-Glucanase Gene Expression in Grapevine Leaves as a Response to Infection With *Botrytis cinera.*" *Am. J. Enol. Vitic.* (2000) 51: 81-87.
Maher et al. "Stress response in alfalfa (*Medicago sativa* L) XVII.: Identification of multiple hydrolases and molecular characterization of an acidic glucanase." *Physiological and Molecular Plant Pathology* (1993) 43: 329-342.
Thimmapuram et al. "Characterization and expression of β-1,3-glucanase genes in peach." *Mol. Genet Genomics* (2001) 265: 469-479.
Castresana et al. "Tissue-Specific and Pathogen-Induced Regulation of a *Nicotiana plumbaginifolia* β-1,3-Glucanase Gene." *The Plant Cell* (Dec. 1990) 2: 1131-1143.
Simmons, Carl R. "The Physiology and Molecular Biology of Plant 1, 3-β-D-Glucanases and 1,3;1,4-β-D-Glucanases." *Critical Reviews in Plant Sciences* (1994) 13(4): 325-387.
Nakamura et al. "Expression of soybean β-1,3-endoglucanase cDNA and effect on disease tolerance in kiwifruit plants." *Plant Cell Reports* (1999) 18: 527-532.
Masoud et al. "Constitutive expression of an inducible β-1, 3-glucanase in alfalfa reduces disease severity caused by the oomycete pathogen *Phytophthora megasperma* f. sp *medicaginis*, but does not reduce disease severity of chitin-containing fungi." *Transgenic Research* (1996) 5: 313-323.
Lusso, J. and J. Kuć. "The effect of sense and antisense expression of the PR-N gene for β-1,3-glucanase on disease resistance of tobacco to fungi and viruses." Physiological and Molecular Plant Pathology (1996) 49: 267-283.
Keen, N. T. and M. Yoshikawa. "β-1,3-Endoglucanase from Soybean Releases Elicitor-Active Carbohydrates from Fungus Cell Walls." *Plant Physiol.* (1983) 71: 460-465.
Sela-Buurlage et al. "Only Specific Tobacco (*Nicotiana tabacum*) Chitinases and β-1,3-Glucanases Exhibit Antifungal Activity." *Plant Physiol.* (1993) 101: 857-863.
Kauffman et al. "Biological function of 'pathogenesis-related' proteins: four PR proteins of tobacco have 1,3-β-glucanase activity." The EMBO Journal (1987) vol. 6. (No. 11): 3209-3212.

*Primary Examiner*—Manjunath N. Rao
(74) *Attorney, Agent, or Firm*—Harness, Dickey & Pierce

(57) ABSTRACT

The present invention relates to a novel nucleic acid encoding a β-1,3-glucanase polypeptide of lily, and an expression vector, host cell and transgenic plant comprising the nucleic acid of the invention. The expression of the nucleic acid of the invention in the plant will enhance resistance against a wide variety of stresses, in particular fungal attack.

8 Claims, 6 Drawing Sheets
(4 of 6 Drawing Sheet(s) Filed in Color)

Fig. 1. shows the protein patterns of the inoculation fluids of *Botrytis* spp. recovered from lily leaves and flowers.

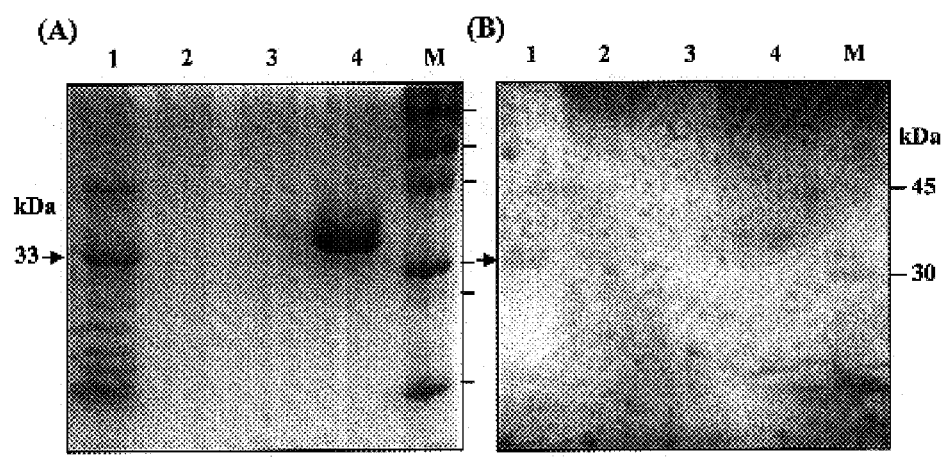
Fig. 2. Detection of β-1,3-glucanase in the inoculation fluid recovered from lily leaves.

Fig. 3. The 2D-electrophoresis analysis of the inoculation fluid of *B. elliptica* recovered from lily leaves.

| | | | | | |
|---|---|---|---|---|---|
| -3 | TTCATGGCAG | CTCAGCACAT | CATCTCCATG | GCTGCCATGG | 37 |
| 38 | CATCCCTCCT | TGTAGTACTC | TCGGCAATCC | CGAGAGGCGT | 77 |
| 78 | GGAATCCATT | GGGGTCTGCA | ATGGAATGGA | CGGTGACAAC | 117 |
| 118 | CTCCCCCAGC | CCGCCGACGT | CGTCAACCTC | TACAAGTCCA | 157 |
| 158 | ACAACATAGC | TGGCATGCGA | CTCTACAGCC | CCGACCAAGC | 197 |
| 198 | CACTCTCCAG | GCCCTCCAGG | GCTCTAACAT | CTACCTCATC | 237 |
| 238 | CTCGACGTCC | CCAACTCCGA | CCTCCAAAAC | ATTGCCTCCG | 277 |
| 278 | ACCAATCCGC | CGCCACCAAC | TGGGTCCAAA | CCAACGTCCA | 317 |
| 318 | AGCCTACCCA | AACGTTGCCT | TCCGATACAT | CGCCGTCGGA | 357 |
| 358 | AACGAAGTCA | TCCCCGGCGG | CCAAGCTCAG | TACGTCCTCC | 397 |
| 398 | CAGCCATGAA | CAACATACAG | TCCGCCCTCT | CCTCTGCCGG | 437 |
| 438 | CCTTCAGAAC | ATCAAGGTCT | CCACATCAGT | CTCCTTCGGC | 477 |
| 478 | GTCGTCGGTA | CCTCATATCC | CCCCTCAGCT | GGCTCCTTCT | 517 |
| 518 | CTTCCGATGC | ATCGTCGACA | TTGGGTCCAA | TCATACAGTT | 557 |
| 558 | TCTAGCCAGC | AATGGCTCCC | CATTACTTGC | CAACATCTAC | 597 |
| 598 | CCCTACTTGA | GCTATGCTGG | CAACTCCGGA | TCCATCGACC | 637 |
| 638 | TCTCATACGC | CCTCTTTACT | GCATCTGGTA | CAGTCGTACA | 677 |
| 678 | GGACGGGTCC | TACGCTTACA | ACAACCTCTT | CGATGCCATG | 717 |
| 718 | GTCGACGCAT | TGTACTCGGC | CCTGGAGAGC | GCCGGAGGGC | 757 |
| 758 | CGAATGTCCC | TGTTGTCGTG | TCGGAGAGTG | GCTGGCCGTC | 797 |
| 798 | AGCGGGCGGG | ACAGCGGCGA | CGGTGTCTAA | TGCGCAGACT | 837 |
| 838 | TACAATTCCA | ATTTGATCAA | CCATGTGGGT | CAGGGGACGC | 877 |
| 878 | CGAAGAGGCC | AGGGGCGATT | GAGACCTACA | TATTTGCCAT | 917 |
| 918 | GTTCAACGAG | GATCAGAAGC | AGCCGCAAGG | GATTGAGAAT | 957 |
| 958 | AACTTTGGGC | TGTTTTACCC | TAACGAACAG | CCTGTCTATT | 997 |
| 998 | CGATCAGCTT | CACTTGAGAA | ATTTGATCAG | ATGAAATATA | 1037 |
| 1038 | <u>AATAAAAGGT</u> | CTTATATTGT | AAGGCAAAGC | TCGTAATTGA | 1077 |
| 1078 | TAGCCATCTA | GTAATATAGC | TCCGGCTAAT | TAAAACTATA | 1117 |
| 1118 | AAATA | | | | 1122 |

Fig. 4. The nucleotide sequence of the full-length cDNA of *LPGlu1*

(incorporating SEQ ID NO: 2).

```
  1 MAAQHIISMA AMASLLVVLS AIPRGVESIG VCNGMDGDNL PQPADVVNLY

51 KSNNIAGMRL YSPDQATLQA LQGSNIYLIL DVPNSDLQNI ASDQSAATNW

101 VQTNVQAYPN VAFRYIAVGN EVIPGGQAQY VLPAMNNIQS ALSSAGLQNI

151 KVSTSVSFGV VGTSYPPSAG SFSSDASSTL GPIIQFLASN GSPLLANIYP

201 YLSYAGNSGS IDLSYALFTA SGTVVQDGSY AYNNLFDAMV DALYSALESA

251 GGPNVPVVVS ESGWPSAGGT AATVSNAQTY NSNLINHVGQ GTPKRPGAIE

301 TYIFAMFNED QKQPQGIENN FGLFYPNEQP VYSISFT
```

Fig. 5. The putative amino acid sequence of LPGlu1 (SEQ ID NO: 1).

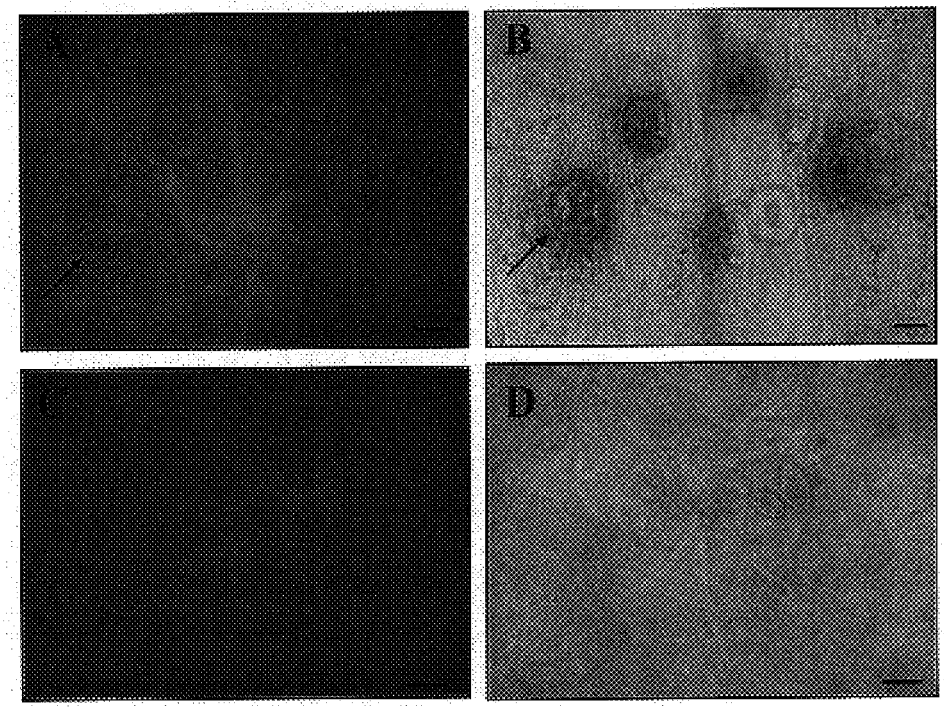
Fig. 6. Comparison of the infection of lily leaves and flowers by *B. elliptica*.

NUCLEIC ACID ENCODING β-1,3-GLUCANASE FROM LILY

BACKGROUND OF THE INVENTION

1. Field of the Invention

The present invention relates to a novel nucleic acid encoding β-1,3-glucanase from lily, the polypeptide encoded therefrom and their applications.

2. Description of the Prior Art

Plants have evolved many mechanisms against pathogen attack such as hypersensitive response (HR), systemic acquired resistance (SAR), and induced systemic resistance (ISR). Plant defense response are generally accompany with the expression of genes encoding pathogenesis-related proteins (PR proteins). Some of the PR proteins have enzymatic activities, such as glucanases. For instance, Kauffmann, S. et al. indicated that four of PR proteins of tobacco have, β-1,3-glucanase activity (Kauffmann et al., 1987, EMBO J. 6: 3209–3212)

Plant β-1,3-glucanase is a hydrolytic enzyme that is abundant in various plant species of monocots and dicots. Some glucanases of plant origin are capable of inhibiting the growth of fungi (Sela-Buurlage et al., 1993, Plant Physiol. 101: 857–863). A purified β-1,3-glucanase from soybean (Keen & Yoshikawa, 1983, Plant Physiol. 71: 460–465) has been shown to be capable of degrading isolated cell walls of fungi in vitro. Recently, overexpression of β-1,3-glucanase in plants was shown to be capable of resisting infection by fungal pathogens (Lusso & Kuć, 1996; Physiol. Mol. Plant Pathol. 49: 267–283; Masoud et al., 1996, Transgenic Res. 5: 313–323; Nakamura et al., 1999, Plant Cell Reports 18: 527–532). In addition, EP 440304 provided plants having improved resistance against pathogenic fungi, which are transformed with at least one gene encoding an intracellular chitinase, or in intra- or extracellular β-1,3-glucanase.

The genes expressing β-1,3-glucanase have been widely studied. Simmons, C. R. disclosed the physiology and molecular biology of plant 1,3-β-D-glucanases and 1,3;1,4-β-D-glucanases (Simmons, C. R., 1994, Critical Rev. Plant Sci. 13:325–387). U.S. Pat. No. 6,066,491 indicated that after a necrotic infection, the enzyme can often be found throughout the plant, including the non-infected parts, in higher concentrations than before infection; Increased synthesis of the enzyme appears to be induced also by microbial elicitors, usually fungal cell wall preparations. Tissue-specific and pathogen-induced regulation of a Nicotiana plumbaginifolia β-1,3-glucanase gene has been found (Castresana et al., 1990, Plant Cell 2: 1131–1143). Moreover, Thimmapuram et al. (2001) and Maher et al. (1993) researched the characterization and expression of β-1,3-glucanase genes in peach and alfalfa, respectively, and found the pathogen-inducible trait (Mol. Gen. Genet. 265:469–479; Physiol. Mol. Plant Pathol. 43: 329–342). Renault et al., 2000 demonstrated the expression of β-1,3-glucanase in grapevine leaves after fungal infection (Am. J. Enol. Vitic. 51: 81–87). In addition, Didierjean L. et al. (1996), reported that β-1,3-glucanase is increased when the corn leaf is stimulated by non-biological conditions (Planta 199:1–8). WO 92/16632disclosed a recombinant DNA sequence derived from soybean which codes for a novel protein with, β-1,3-glucanase activity.

It is still a need to further develop new nucleic acid expressing β-1,3-glucanase.

SUMMARY OF THE INVENTION

The present invention provides an isolated nucleic acid sequence encoding a polypeptide having β-1,3-glucanase activity, wherein the polypeptide is selected from the group consisting of: (a) a polypeptide having an amino acid sequence shown in SEQ ID NO: 1; and (b) a polypeptide encoded by a nucleic acid sequence which hybridizes under high stringency conditions with the nucleotide sequence of SEQ ID NO:2.

The present invention provides a vector comprising the isolated nucleic acid molecule of the invention.

The present invention also provides a host cell comprising the isolated nucleic acid molecule of the invention.

The present invention also provides a transgenic plant, which is transformed with the isolated nucleic acid molecule of the invention.

The present invention further provides an isolated polypeptide, which is selected from the group consisting of: (a) a polypeptide having an amino acid sequence shown in SEQ ID NO: 1; and (b) a polypeptide which is encoded by a nucleic acid sequence which hybridizes under high stringency conditions with the nucleotide sequence of SEQ ID NO:2.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the protein patterns of the inoculation fluids of Botrytis spp. recovered from lily leaves and flowers.

FIG. 2 shows the detection of β-1,3-glucanase in the inoculation fluid recovered from lily leaves.

FIG. 3 shows the 2D-electrophoresis analysis of the inoculation fluid of B. elliptica recovered from lily leaves.

FIG. 4 shows the nucleotide sequence of the full-length cDNA of LPGlu1.

FIG. 5 shows the putative amino acid sequence of LPGlu1.

FIG. 6 shows the comparison of the infection of lily leaves and flowers by B. elliptica.

DETAILED DESCRIPTION OF THE INVENTION

The present invention provides a novel nucleic acid encoding β-1,3-glucanase from lily, the polypeptide encoded therefrom and their applications.

Nucleic Acid and the Polypeptide Encoded Therefrom

One aspect of the invention is to provide an isolated nucleic acid sequence encoding a polypeptide having β-1,3-glucanase activity, wherein the polypeptide is selected from the group consisting of:

(a) a polypeptide having an amino acid sequence shown in SEQ ID NO: 1; and (b) a polypeptide encoded by a nucleic acid sequence which hybridizes under high stringency conditions with the nucleotide sequence of SEQ ID NO:2.

As used herein, the term "nucleic acid" refers to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). As used herein "isolated nucleic acid" refers to a nucleic acid substantially or essentially free from components which normally accompany or interact with it as found in its naturally occurring environment; or (2) if the nucleic acid is in its natural environment, the nucleic acid has been synthetically (non-naturally) altered by deliberate human intervention to a composition and/or placed at a locus in the cell (e.g., genome or subcellular organelle) not native to a nucleic acid found in that environment.

As used herein, the term "polynucleotide" refers to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s).

As used herein, the phrase "hybridizes under stringent conditions" refers to the formation of a double-stranded duplex from two single-stranded nucleic acids. The region of double-strandedness can include the full-length of one or both of the single-stranded nucleic acids, or all of one single-stranded nucleic acid and a subsequence of the other single-stranded nucleic acid, or the region of double-strandedness can include a subsequence of each nucleic acid. High stringency conditions when used in reference to nucleic acid hybridization comprise conditions equivalent to binding or hybridization at 68° C. in a solution consisting of 5×SSPE, 1% SDS, 5× Denhardt's reagent and 100 µg/ml denatured salmon sperm DNA followed by washing in a solution comprising 0.1 SSPE, and 0.1% SDS at 68° C. when a probe of about 100 to about 1000 nucleotides in length is employed, or the above-mentioned conditions with 50% formamide at 42° C. High stringency washes can include 0.1×SSC to 0.2×SSC, 1% SDS, 65° C., 15–20 min. An example of stringent wash conditions for a Southern blot of such nucleic acids is a 0.2×SSC wash at 65° C. for 15 minutes (see, Sambrook et al., Molecular Cloning—A Laboratory Manual (2.sup.nd ed.) Vol. 1–3, Cold Spring Harbor Laboratory, Cold Spring Harbor Press, NY, 1989, for a description of SSC buffer). Other exemplary high stringency hybridization conditions include, for example, 7% SDS, 0.25 M sodium phosphate buffer, pH 7.0–7.2, 0.25 M sodium chloride at 65° C.–68° C. or the above-mentioned conditions with 50% formamide at 42° C. Exemplary medium stringency conditions are as described above for high stringency except that 35% formamide at 42° C. is used, and the washes are carried out at 55° C.

According to the invention, the isolated nucleic acid molecules which encode a polypeptide having β-1,3-glucanase activity include genomic sequences which encode a glucanase and which direct and regulate the transcriptional and translational expression of the β-1,3-glucanase coding sequences, and cDNA sequences which encode a polypeptide having β-1,3-glucanase activity.

Preferably, the nucleic acid of the invention comprises a polynucleotide that encodes a polypeptide having an amino acid sequence shown in SEQ ID NO: 1. Preferably, the nucleic acid of the invention comprises a polynucleotide that encodes a polypeptide which is encoded by a nucleic acid sequence which hybridizes under high stringency conditions with the nucleotide sequence of SEQ ID NO:2. More preferably, the nucleic acid of the invention comprises a polynucleotide having the sequence as shown in SEQ ID NO: 2. According to the invention, the preferred polynucleotide of SEQ ID NO: 2 includes 1,011 nucleotides.

Another aspect of the invention is to provide an isolated polypeptide, which is selected from the group consisting of: (a) a polypeptide having an amino acid sequence shown in SEQ ID NO: 1; and (b) a polypeptide which is encoded by a nucleic acid sequence which hybridizes under high stringency conditions with the nucleotide sequence of SEQ ID NO:2. Preferably, the polypeptide encoded by the isolated nucleic acid of the invention comprises amino acid sequence of SEQ ID NO: 1.

As used herein, the terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids.

According to the invention, the sequence of SEQ ID NO: 2 codes for 337 amino acids with a calculated molecular weight of 35.328. The embodiment polypeptide of the invention is isolated form lily, which is a pathogen-induced glucanase. The N-terminal sequence of the isolated glucanase protein contains amino acid residues of MDGDNLPQ-PADVVNLY (SEQ ID NO: 3). Therefore, the new polypeptide of the invention is named LPGlu1 (lily pathogen-induced glucanase 1).

According to the invention, the LPGlu1 of the invention is considered as an acidic isoform of β-1,3-glucanase with a pI value about 4.0. As known, acidic glucanase plays a role to release β-glucan oligomers, which may act as elicitors to induce plant resistance (Ebel & Mithöfer, 1998, Planta 206:335–348) Acidic glucanase is usually induced systemically by pathogen attack and is a marker of SA-induced plant defense (Henning et al., 1993, Plant J. 4: 481–493) Therefore, it is believed that the LPGlu1 of the invention can be applied to enhance plant defense against stresses, especially fungal attack.

Expression Vector and Host System

A further aspect of the invention is to provide a vector, which comprises the isolated nucleic acid of the invention.

As used herein, "vector" includes reference to a nucleic acid used in transfection or transformation of a host cell and into which can be inserted a polynucleotide. Vectors are often replicons. Expression vectors permit transcription and translation of a nucleic acid inserted therein.

Another further aspect of the invention is to provide a host cell containing the vector containing the isolated nucleic acid of the invention. The term "host cell" refers to, for example, microorganisms including prokaryotic (Eubacteria and Archea) microorganisms (e.g., E. coli and cyanobacteria) and eukaryotic microorganisms (e.g., yeast), and plant cells, which can be used as a recipient for introduction of a vector.

In order to express a nucleic acid molecule of the invention, the isolated nucleic acids encoding the polypeptides of the invention, can be inserted into an appropriate expression vector, i.e., a vector which contains the necessary elements for the transcription and translation of the inserted coding sequence. According to the invention, methods well known to those skilled in the art can be used to construct expression vectors containing sequences encoding the β-1,3-glucanase polypeptides of the invention and appropriate transcriptional and translational control elements. These methods include in vitro recombinant DNA techniques, synthetic techniques, and in vivo genetic recombination. Preferred vectors for isolation and multiplication are plasmids which can be propagated in a suitable host microorganism, for example in *E. coli*. Preferred vectors for transformation are those useful for transformation of plant cells or of *Agrobacterium*. For *Agrobacterium*-mediated transformation, the preferred vector is a Ti-plasmid derived vector. For the direct DNA transfer into protoplasts, any of the mentioned vectors may be used. Appropriate vectors which can be utilized as starting materials are known in the art.

According to the invention, a number of host systems can be utilized to contain and express sequences encoding the β-1,3-glucanase polypeptides of the invention. A variety of techniques are available for the introduction of the nucleic acid fragment into a host cell. However, the particular manner of introduction of the nucleic acid fragment into the host cell is not critical to the practice of the present invention, and methods that provide for efficient transformation can be employed. Preferably, the host cell is a bacterial cell or a plant cell. More preferably, the host cell is an *Agrobacterium* cell.

Transgenic Plants

The present invention also relates to a transgenic plant, which is transformed with an isolated nucleic acid molecule of the invention.

The term "transgenic" refers to any cell, cell line, tissue, plant part or plant, the genotype of which has been altered by the presence of an exogenous coding region. Typically, the exogenous coding region was introduced into the genotype by a process of genetic engineering, or was introduced into the genotype of a parent cell or plant by such a process and is subsequently transferred to later generations by sexual crosses or asexual propagation.

Various methods are known in the art to accomplish the genetic transformation of plants and plant tissues (i.e., the stable introduction of foreign DNA into plants). These include transformation by *Agrobacterium* species and transformation by direct gene transfer. Typically, methods of making a transgenic plant of the invention involve the transformation of a cell of a plant with isolated nucleic acid molecule, which encodes β-1,3-glucanase polypeptides of the invention. The nucleic acid fragment is typically carried by a vector. The vector includes those as described herein. In a plant cell, the vector can replicate independently, i.e., extrachromosomally, which can allow for a large number of vectors to be maintained and potentially result in higher polypeptide production, or can be integrated into the genomic DNA. Preferably the vector is integrated into the genomic DNA of a plant cell.

The transgenic plant of the invention has a resistance to a wide variety of pathogen attack through the expression of the new gene of the invention. Particularly, the transgenic plant has a resistance to the stress; more particularly, resistance to fungal disease, such as *Botrytis* blight and gray mold.

Utility

The isolated nucleic acid molecule of the invention encodes β-1,3-glucanase polypeptide that confers plant disease resistance. The β-1,3-glucanase is a pathogen-inducible "defense-related protein." The β-1,3-glucanase can degrade the cell wall of pathogens and result in the release of elicitors activating the plant defense system. The elicitor refers to the compound inducing the production of phytoalexins in plants and other defense reactions such as lignin and PR protein production. The expression of the nucleic acid of the invention in the plant will increase the resistance against stresses, preferably fungal attack. In particular, the expression of the nucleic acid of the invention can suppress infection by *Botrytis* pathogens.

According to the invention, the isolated nucleic acid molecule of the invention can be used as the plant defense marker to select the cultivars having resistance to pathogens. The plant cultivars against pathogens can be selected by detecting the expression of the nucleic acid of the invention.

The expression of the nucleic acids of the present invention also can be used in identifying compounds that increase the enzymatic activity of β-1,3-glucanase of the present invention.

According to the invention, the polypeptide encoded by the nucleic acid of the invention can catalyze the degradation of glucan. Moreover, the polypeptide of the invention is capable of degrading the cell wall of fungi and thus can be used as an antifungal compound.

The following examples are offered by way of illustration and not by way of limitation.

EXAMPLES

Example 1 Isolation of β-1,3-Glucanase of the Invention

Plant Material

Lily bulbs (oriental hybrid 'Star Gazer') were planted in a mixture of pot medium and perlite (3:1 v/v). The plants were cultivated in the semi-open house covered with a shading screen for 25–45 days depending on the weather condition.

Inoculation of *B. elliptica* and *B. cinerea*

Spore suspensions of *B. elliptica* B061-1-1 and *B. cinerea* B071-1-1 were inoculated on the detached lily leaves and flowers (6 drops on each leaf and flower, 20 μl each drop). The lily leaves of middle part ($8^{th}$ to $10^{th}$ from the top) were detached and placed with adaxial surface up in the glass Petri dish with wet cotton on the cut surface of the vein of leaves to keep moisture. The lily flowers were detached after flowering for 1–2 days and placed in glass Petri dish for inoculation.

Recovery of the Inoculation Fluid

The inoculation fluid of *B. elliptica* B061-1-1 and and *B. cinerea* B071-1-1 was recovered from the inoculated leaves or flowers and stored in 0.2 μg/ml protease inhibitor APMSF solution at −20° C.

SDS-PAGE

The recovered inoculation fluids of *B. elliptica* and *B. cinerea* on lily leaves and flowers appeared reddish brown. The red brown substances could be removed after passage through Centricon YM-K-3 column (cut off 3-kDa molecules) (Amicon, Bedford, Mass., USA). The recovered inoculation fluids (about 200 μl) were concentrated five folds by lyophilization before SDS-PAGE.

SDS-PAGE electrophoresis was performed under denaturing conditions according to Laemmli (Laemmli, U. K. 1970, Nature 227: 680–685), using a 4% (w/v) stacking gel and 12% running gel and performed under 120 V constant voltage. Proteins in the gel were stained with Coomassie Brilliant Blue (CBR-250) according to Bradford's method (Bradford, M. M. 1976, Anal. Biochem. 72: 248–254), wherein the M is prestained protein molecular weight marker (GIBCoBRL). SDS-PAGE analysis revealed protein in the recovered inoculation fluids of *B. elliptica* and *B.*

*cinera* from lily (FIG. 1). At least four protein bands corresponding to the estimated molecular mass of 49, 33, 27 and 16 kDa were shown in the inoculation fluids of *B. elliptica* recovered 72 hr (FIG. 1A, lane 2) and 96 hr (FIG. 1A, lane 5) after inoculation. None of the protein bands were detected in the inoculation fluids of *B. cinerea* recovered 72 hr (FIG. 1A, lane 1) and 96 hr (FIG. 1A, lane 4) after inoculation. Inoculation solutions deposited on the surface of lily leaves and recovered 72 hr (FIG. 1A, lane 3) and 96 hr (FIG. 1A, lane 6) after inoculation were the controls. Inoculation fluids of *B. elliptica* on lily flowers recovered 12 hr (FIG. 1B, lane 2), 24 hr (FIG. 1B, lane 5) and 48 hr (FIG. 1B, lane 7) after inoculation did not show visible protein bands, same as that shown in the inoculation fluids of *B. cinerea* (FIG. 1B, lane 1, 4 and 8). Inoculation solutions deposited on the surface of lily flowers and recovered 12 hr (FIG. 1B, land 3), 24 hr (FIG. 1B, lane 6) and 48 hr (FIG. 1B, lane 9) after inoculation were the controls.

N-terminal Sequencing

After electrophoresis, the gel containing estimated 33-kDa protein band was equilibrated with 100 ml buffer (50 mM boric acid, 0.1% (w/v) SDS, adjusted to pH 8.0 with 1 M NaOH) for 1 hr and then the proteins were transferred onto a polyvinyllidenedifluoride (PVDF) membrane in a Tris-boric acid (50 mM each) transfer buffer, at 35 V constant voltage overnight. After blotting, the PVDF membrane was washed with distilled water and stained for 5 minutes in a mixture containing 0.1% (w/v) naphthol blue black, 45% (v/v) methanol and 7% (v/v) acetic acid. The estimated 33-kDa protein band was sliced out, destained in distilled water, and air dried. The protein-containing PVDF strip was stored at 4° C. and used for N-terminal sequencing.

The N-terminal sequence of this estimated 33-kDa protein showed a successive 16 amino acid residues of MDGDN-LPQPADVVNLY (SEQ ID. NO: 3) and 6 ambiguous non-contiguous amino acid residues. The successive 16 residues are 86–93% homologous to that of β-1,3-glucanase protein from cotton and *Arabidopsis*. The 33-kDa protein was named LPGlu1 (lily pathogen-induced glucanase 1).

In-gel Activity Staining of β-1,3-glucanase

Two method of in-gel activity staining of β-1,3-glucanase were performed. One was modified from that described by Shimoni, M. 1994, Anal. Biochem. 220:36–38. The other method was performed in SDS-PAGE system as described by Trudel et al. 1998, Electrophoresis 19:1788–1792. 2,3,5-triphenyltetrazolium chloride and laminarin (2%) were used as developing agent and substrate, respectively. The gel obtained after SDS-PAGE was incubated in renaturing solution (0.5% Triton X-100 in 10 mM phosphate buffer pH 6.0) to increase the efficacy of protein renaturation. The glucanase activity was identified by the second method of in-gel activity staining (see FIG. 2). FIG. 2A shows the in-gel activity staining of β-1,3-glucanase in the inoculation fluids of *B. elliptica* (lane 1) and *B. cinerea* (lane 2) recovered from lily leaves. Inoculation solution was deposited as mock inoculation (FIG. 2A, lane 3). The β-1,3-glucanase from *Streptomyces sioyaensis* was used as a positive control (FIG. 2A, lane 4).

FIG. 2B shows the gel of SDS-PAGE corresponding to FIG. 2A, which was stained with Coomassie Brilliant Blue (CBR-250), wherein the M is the low molecular weight protein marker, the bars from up to bottom corresponding to 97, 66, 45, 30, 21 and 14 kDa).

Two-Dimensional Electrophoresis

Iso-electric focusing electrophoresis (IEF) was performed with inoculation fluid of *B. elliptica* recovered from lily leaves. An amount of 200 μg protein was assayed according to the manual provided by manufacture (Bio-Rad). The 2D-electrophoresis analysis showed that LPGlu1 (marked with a circle) is an acidic isoforms of β-1,3-glucanase with pI value about 4.0 (see FIG. 3).

Example 2 Cloning of the cDNA of the Invention Coding for β-1,3-Glucanase

In order to clone the full length cDNA of LPGlu1 gene from lily, the RT-PCR (reverse transcription-polymerase chain reaction) and RACE (rapid amplification of cDNA ends) method were performed.

RT-PCR

The total RNA of the β-1,3-glucanase was extracted according to Ausubel et al. 1995, Currect Protocols in Molecular Biology. John Wiley and Sons, Inc. USA. Then, mRNA was extracted using Oligotex™ kit Handbook (QIAGEN). According to the alignment of N-terminal sequence of recovered 33-kDa protein and the amino acid sequences with high homology, degenerate primers were designed and used in RT-PCR to amplify the cDNA coding for β-1,3-glucanase from lily. The PCR thermal cycles were 95° C. 3 min, 1 cycle; 95° C. 1 min, 55° C. 1 min, 30 cycles; 72° C. 10 min, 1 cycle, using a RoboCycler temperature cycler (Stratagene).

RACE

RACE system was performed by using Marathon™ cDNA amplification kit (Clontech). RACE PCR program was 94° C. 1 min, 1 cycle; 94° C. 30 sec, 72° C. 3 min, 5 cycles; 94° C. 30 sec, 70° C. 30 sec, 72° C. 3 min, 5 cycles; 94° C. 30 sec, 68° C. 30 sec, 72° C. 2 min, 20 cycles.

In RT-PCR, 3' RACE and 5' RACE, three major bands of DNA (700, 750 and 300 bp, respectively) were obtained. After cloning, the DNAs were sequenced and compiled for full-length cDNA sequence. The full-length cDNA of LPGlu1 (see FIG.4) includes a predicted open reading frame of 1,011 bp encoding 337 amino acid residues with a calculated molecular weight of 35.328 (see FIG. 4 and 5). As shown in FIG. 4, the blocks indicate the predicted start codon ATG and stop codon TGA. A predicted polyadenylation signal sequence is underlined. A predicted cleavage site of signal peptidase was found between serine-isoleucine amino acids corresponding to 28–29 residues.

Example 3 Observation of Infection Processes on the Surface of Lily Leaves and Flowers under Epifluorescence Microscope Inoculated lily leaves and flowers were autoclaved for 15 min at 121° C. in 30–50 ml of 1 M KOH, and rinsed in distilled water for three times. Then, specimens were mounted on glass slides in several drops of staining solution and examined under epiflurescence microscope (Leica DM IL microscope, Wetzlar, Germany). The staining solution (0.05% aniline blue in 0.067 M $K_2HPO_4$, pH 9.0) was prepared at least two hours before use (Hood and Shew 1996, Phytopathology 86:704–708). The microscope is equipped for epifluorescence microscopy with a Mercury burner and G340–380 nm exciter:LP (long pass) 425 nm fluorescence filters. The photographs were taken with digital camera (Nikon CoolPIX990, Tokyo, Japan).

In the microscopic observation of the infection process of *B. elliptica* on lily leaves and flowers, brown mini-necrosis appeared in half of the observed penetration sites and frequently in the plant cells around the growing hyphae of *B. elliptica* on lily leaves. However, the necrosis did not appear in *B. elliptica*-infected lily flowers. On the other hand, mini-necrosis appeared only in a few of guard cells near the germinated spores of *B. cinera* on lily leaves, and not in the

*B. cinerea*-infected lily flowers. Cell death (indicated by arrows) appeared to limit the infection of lily leaves by *B. elliptica*. Dead cells might stop the growth of fungal hyphae (FIG. 6A and 6B). Cell death did not appear on lily flowers during *B. elliptica* attack (FIG. 6C and 6D). Pictures were photographed under bright-field microscope (FIG. 6B and 6D) and fluorescence microscope (FIG. 6A and 6C) 12 hr after inoculation, respectively (Bar=24.5 μm).

What is claimed is:

1. An isolated nucleic acid sequence encoding a polypeptide having β-1,3-glucanase activity, wherein the polypeptide is selected from the group consisting of:
   (a) a polypeptide having the amino acid sequence of SEQ ID NO: 1; and
   (b) a polypeptide which is encoded by a nucleic acid sequence which hybridizes under high stringency conditions with the nucleotide sequence of SEQ ID NO:2.

2. The isolated nucleic acid molecule of claim 1, which has the sequence of SEQ ID NO: 2.

3. A vector comprising the isolated nucleic acid molecule as claimed in claim 1.

4. The vector of claim 3, wherein the isolated nucleic acid has the sequence of SEQ ID NO: 2.

5. An isolated host cell comprising the vector of claim 3.

6. The host cell of claim 5, wherein the host cell is a bacterial cell or a plant cell.

7. The host cell of claim 6, wherein the bacterial cell is an *Agrobacterium* cell.

8. The host cell of claim 6, wherein the host cell is a plant cell.

* * * * *

```
                       SEQUENCE LISTING

<160> NUMBER OF SEQ ID NOS: 3

<210> SEQ ID NO 1
<211> LENGTH: 337
<212> TYPE: PRT
<213> ORGANISM: Lily

<400> SEQUENCE: 1

Met Ala Ala Gln His Ile Ile Ser Met Ala Met Ala Ser Leu Leu
1               5                   10                  15

Val Val Leu Ser Ala Ile Pro Arg Gly Val Glu Ser Ile Gly Val Cys
            20                  25                  30

Asn Gly Met Asp Gly Asp Asn Leu Pro Gln Pro Ala Asp Val Val Asn
        35                  40                  45

Leu Tyr Lys Ser Asn Asn Ile Ala Gly Met Arg Leu Tyr Ser Pro Asp
    50                  55                  60

Gln Ala Thr Leu Gln Ala Leu Gln Gly Ser Asn Ile Tyr Leu Ile Leu
65                  70                  75                  80

Asp Val Pro Asn Ser Asp Leu Gln Asn Ile Ala Ser Asp Gln Ser Ala
                85                  90                  95

Ala Thr Asn Trp Val Gln Thr Asn Val Gln Ala Tyr Pro Asn Val Ala
            100                 105                 110

Phe Arg Tyr Ile Ala Val Gly Asn Glu Val Ile Pro Gly Gly Gln Ala
        115                 120                 125

Gln Tyr Val Leu Pro Ala Met Asn Asn Ile Gln Ser Ala Leu Ser Ser
    130                 135                 140

Ala Gly Leu Gln Asn Ile Lys Val Ser Thr Ser Val Ser Phe Gly Val
145                 150                 155                 160

Val Gly Thr Ser Tyr Pro Pro Ser Ala Gly Ser Phe Ser Ser Asp Ala
                165                 170                 175

Ser Ser Thr Leu Gly Pro Ile Ile Gln Phe Leu Ala Ser Asn Gly Ser
            180                 185                 190

Pro Leu Leu Ala Asn Ile Tyr Pro Tyr Leu Ser Tyr Ala Gly Asn Ser
        195                 200                 205

Gly Ser Ile Asp Leu Ser Tyr Ala Leu Phe Thr Ala Ser Gly Thr Val
    210                 215                 220

Val Gln Asp Gly Ser Tyr Ala Tyr Asn Asn Leu Phe Asp Ala Met Val
225                 230                 235                 240

Asp Ala Leu Tyr Ser Ala Leu Glu Ser Ala Gly Gly Pro Asn Val Pro
                245                 250                 255

Val Val Val Ser Glu Ser Gly Trp Pro Ser Ala Gly Gly Thr Ala Ala
            260                 265                 270

Thr Val Ser Asn Ala Gln Thr Tyr Asn Ser Asn Leu Ile Asn His Val
        275                 280                 285

Gly Gln Gly Thr Pro Lys Arg Pro Gly Ala Ile Glu Thr Tyr Ile Phe
    290                 295                 300

Ala Met Phe Asn Glu Asp Gln Lys Gln Pro Gln Gly Ile Glu Asn Asn
305                 310                 315                 320

Phe Gly Leu Phe Tyr Pro Asn Glu Gln Pro Val Tyr Ser Ile Ser Phe
```

-continued

```
                 325              330              335
Thr
```

<210> SEQ ID NO 2
<211> LENGTH: 1125
<212> TYPE: DNA
<213> ORGANISM: Lily

<400> SEQUENCE: 2

```
ttcatggcag ctcagcacat catctccatg gctgccatgg catccctcct tgtagtactc      60
tcggcaatcc cgagaggcgt ggaatccatt ggggtctgca atggaatgga cggtgacaac     120
ctcccccagc ccgccgacgt cgtcaacctc tacaagtcca acaacatagc tggcatgcga     180
ctctacagcc ccgaccaagc cactctccag gccctccagg gctctaacat ctacctcatc     240
ctcgacgtcc ccaactccga cctccaaaac attgcctccg accaatccgc cgccaccaac     300
tgggtccaaa ccaacgtcca agcctaccca aacgttgcct tccgatacat cgccgtcgga     360
aacgaagtca tccccggcgg ccaagctcag tacgtcctcc cagccatgaa caacatacag     420
tccgccctct cctctgccgg ccttcagaac atcaaggtct ccacatcagt ctccttcggc     480
gtcgtcggta cctcatatcc cccctcagct ggctccttct cttccgatgc atcgtcgaca     540
ttgggtccaa tcatacagtt tctagccagc aatggctccc cattacttgc caacatctac     600
ccctacttga gctatgctgg caactccgga tccatcgacc tctcatacgc cctctttact     660
gcatctggta cagtcgtaca ggacgggtcc tacgcttaca caacctctt cgatgccatg     720
gtcgacgcat tgtactcggc cctggagagc gccggagggc cgaatgtccc tgttgtcgtg     780
tcggagagtg gctggccgtc agcgggcggg acagcggcga cggtgtctaa tgcgcagact     840
tacaattcca atttgatcaa ccatgtgggt caggggacgc cgaagaggcc aggggcgatt     900
gagacctaca tatttgccat gttcaacgag gatcagaagc agccgcaagg gattgagaat     960
aactttgggc tgttttaccc taacgaacag cctgtctatt cgatcagctt cacttgagaa    1020
atttgatcag atgaaatata aataaaaggt cttatattgt aaggcaaagc tcgtaattga    1080
tagccatcta gtaatatagc tccggctaat taaaactata aaata                   1125
```

<210> SEQ ID NO 3
<211> LENGTH: 16
<212> TYPE: PRT
<213> ORGANISM: Lily

<400> SEQUENCE: 3

```
Met Asp Gly Asp Asn Leu Pro Gln Pro Ala Asp Val Val Asn Leu Tyr
1               5                   10                  15
```